(12) United States Patent
George et al.

(10) Patent No.: US 11,839,404 B2
(45) Date of Patent: Dec. 12, 2023

(54) SURGICAL ACCESS ASSEMBLY HAVING PRE-FILLED AIR CHAMBER

(71) Applicant: Covidien LP, Mansfield, MA (US)

(72) Inventors: Sabastian K. George, Hyderabad (IN); Oksana Buyda, East Haven, CT (US)

(73) Assignee: Covidien LP, Mansfield, MA (US)

( * ) Notice: Subject to any disclaimer, the term of this patent is extended or adjusted under 35 U.S.C. 154(b) by 543 days.

(21) Appl. No.: 16/941,222

(22) Filed: Jul. 28, 2020

(65) Prior Publication Data
US 2022/0031352 A1  Feb. 3, 2022

(51) Int. Cl.
*A61B 17/34* (2006.01)

(52) U.S. Cl.
CPC ...... *A61B 17/3423* (2013.01); *A61B 17/3498* (2013.01); *A61B 2017/3425* (2013.01); *A61B 2017/3486* (2013.01)

(58) Field of Classification Search
CPC ............ A61B 17/3417; A61B 17/3421; A61B 17/3423; A61B 2017/3441; A61B 2017/3482; A61B 2017/3484; A61B 2017/3486; A61B 2017/3492; A61M 25/04; A61M 25/10181; A61J 15/0042
See application file for complete search history.

(56) References Cited

U.S. PATENT DOCUMENTS

| | | | |
|---|---|---|---|
| 397,060 A | 1/1889 | Knapp | |
| 512,456 A | 1/1894 | Sadikova | |
| 1,213,005 A | 1/1917 | Pillsbury | |
| 2,912,981 A | 11/1959 | Keough | |
| 2,936,760 A | 5/1960 | Gains | |
| 3,039,468 A | 6/1962 | Price | |
| 3,050,066 A | 8/1962 | Koehn | |
| 3,253,594 A | 5/1966 | Matthews et al. | |
| 3,397,699 A | 8/1968 | Kohl | |
| 3,545,443 A | 12/1970 | Ansari et al. | |
| 3,713,447 A | 1/1973 | Adair | |
| 3,774,596 A | 11/1973 | Cook | |
| 3,800,788 A | 4/1974 | White | |

(Continued)

FOREIGN PATENT DOCUMENTS

| | | |
|---|---|---|
| EP | 0480653 A1 | 4/1992 |
| EP | 0610099 A2 | 8/1994 |

(Continued)

OTHER PUBLICATIONS

Extended European Search Report dated Nov. 24, 2021 issued in corresponding EP Appln. No. 21187343.5.

*Primary Examiner* — Diane D Yabut
(74) *Attorney, Agent, or Firm* — Carter, DeLuca & Farrell LLP

(57) ABSTRACT

A surgical access assembly includes an elongated cannula member having a proximal end portion and a distal end portion, a balloon anchor coupled to the distal end portion of the elongated cannula member, a sleeve of the balloon anchor extending proximally along an outer surface of the elongated cannula member, a chamber defined between the sleeve of the balloon anchor and the outer surface of the elongated cannula member, and a first collar is coupled to the elongated cannula member. The first collar is slidable along the elongated cannula member and engageable with the sleeve of the balloon anchor.

15 Claims, 4 Drawing Sheets

(56) References Cited

U.S. PATENT DOCUMENTS

| | | | |
|---|---|---|---|
| 3,882,852 A | 5/1975 | Sinnreich |
| 3,896,816 A | 7/1975 | Mattler |
| 3,961,632 A | 6/1976 | Moossun |
| RE29,207 E | 5/1977 | Bolduc et al. |
| 4,083,369 A | 4/1978 | Sinnreich |
| 4,217,889 A | 8/1980 | Radovan et al. |
| 4,243,050 A | 1/1981 | Littleford |
| 4,276,874 A | 7/1981 | Wolvek et al. |
| 4,312,353 A | 1/1982 | Shahbabian |
| 4,327,709 A | 5/1982 | Hanson et al. |
| 4,345,606 A | 8/1982 | Littleford |
| 4,411,654 A | 10/1983 | Boarini et al. |
| 4,416,267 A | 11/1983 | Garren et al. |
| 4,490,137 A | 12/1984 | Moukheibir |
| 4,496,345 A | 1/1985 | Hasson |
| 4,574,806 A | 3/1986 | McCarthy |
| 4,581,025 A | 4/1986 | Timmermans |
| 4,596,554 A | 6/1986 | Dastgeer |
| 4,596,559 A | 6/1986 | Teischhacker |
| 4,608,965 A | 9/1986 | Anspach, Jr. et al. |
| 4,644,936 A | 2/1987 | Schiff |
| 4,654,030 A | 3/1987 | Moll et al. |
| 4,685,447 A | 8/1987 | Iversen et al. |
| 4,701,163 A | 10/1987 | Parks |
| 4,738,666 A | 4/1988 | Fuqua |
| 4,769,038 A | 9/1988 | Bendavid et al. |
| 4,772,266 A | 9/1988 | Groshong |
| 4,779,611 A | 10/1988 | Grooters et al. |
| 4,784,133 A | 11/1988 | Mackin |
| 4,793,348 A | 12/1988 | Palmaz |
| 4,798,205 A | 1/1989 | Bonomo et al. |
| 4,800,901 A | 1/1989 | Rosenberg |
| 4,802,479 A | 2/1989 | Haber et al. |
| 4,813,429 A | 3/1989 | Eshel et al. |
| 4,840,613 A | 6/1989 | Balbierz |
| 4,854,316 A | 8/1989 | Davis |
| 4,861,334 A | 8/1989 | Nawaz |
| 4,865,593 A | 9/1989 | Ogawa et al. |
| 4,869,717 A | 9/1989 | Adair |
| 4,888,000 A | 12/1989 | McQuilkin et al. |
| 4,899,747 A | 2/1990 | Garren et al. |
| 4,917,668 A | 4/1990 | Haindl |
| 4,931,042 A | 6/1990 | Holmes et al. |
| 4,955,895 A | 9/1990 | Sugiyama et al. |
| 5,002,557 A | 3/1991 | Hasson |
| 5,009,643 A | 4/1991 | Reich et al. |
| 5,030,206 A | 7/1991 | Lander |
| 5,030,227 A | 7/1991 | Rosenbluth et al. |
| 5,074,871 A | 12/1991 | Groshong |
| 5,098,392 A | 3/1992 | Fleischhacker et al. |
| 5,104,383 A | 4/1992 | Shichman |
| 5,116,318 A | 5/1992 | Hillstead |
| 5,116,357 A | 5/1992 | Eberbach |
| 5,122,122 A | 6/1992 | Allgood |
| 5,122,155 A | 6/1992 | Berbach |
| 5,137,512 A | 8/1992 | Burns et al. |
| 5,141,494 A | 8/1992 | Danforth et al. |
| 5,141,515 A | 8/1992 | Eberbach |
| 5,147,302 A | 9/1992 | Euteneuer et al. |
| 5,147,316 A | 9/1992 | Castillenti |
| 5,147,374 A | 9/1992 | Fernandez |
| 5,158,545 A | 10/1992 | Trudell et al. |
| 5,159,925 A | 11/1992 | Neuwirth et al. |
| 5,163,949 A | 11/1992 | Bonutti |
| 5,176,692 A | 1/1993 | Wilk et al. |
| 5,176,697 A | 1/1993 | Hasson et al. |
| 5,183,463 A | 2/1993 | Debbas |
| 5,188,596 A | 2/1993 | Condon et al. |
| 5,188,630 A | 2/1993 | Christoudias |
| 5,195,507 A | 3/1993 | Bilweis |
| 5,201,742 A | 4/1993 | Hasson |
| 5,201,754 A | 4/1993 | Crittenden et al. |
| 5,209,725 A | 5/1993 | Roth |
| 5,215,526 A | 6/1993 | Deniega et al. |
| 5,222,970 A | 6/1993 | Reeves |
| 5,226,890 A | 7/1993 | Ianniruberto et al. |
| 5,232,446 A | 8/1993 | Arney |
| 5,232,451 A | 8/1993 | Freitas et al. |
| 5,234,454 A | 8/1993 | Bangs |
| 5,250,025 A | 10/1993 | Sosnowski et al. |
| 5,258,026 A | 11/1993 | Johnson et al. |
| 5,269,753 A | 12/1993 | Wilk |
| 5,290,249 A | 3/1994 | Foster et al. |
| 5,308,327 A | 5/1994 | Heaven et al. |
| 5,309,896 A | 5/1994 | Moll et al. |
| 5,314,443 A | 5/1994 | Rudnick |
| 5,318,012 A | 6/1994 | Wilk |
| 5,330,497 A | 7/1994 | Freitas et al. |
| 5,342,307 A | 8/1994 | Euteneuer et al. |
| 5,346,504 A | 9/1994 | Ortiz et al. |
| 5,359,995 A | 11/1994 | Sewell, Jr. |
| 5,361,752 A | 11/1994 | Moll et al. |
| 5,370,134 A | 12/1994 | Chin et al. |
| 5,383,889 A | 1/1995 | Warner et al. |
| 5,397,311 A | 3/1995 | Walker et al. |
| 5,402,772 A | 4/1995 | Moll et al. |
| 5,407,433 A | 4/1995 | Loomas |
| 5,431,173 A | 7/1995 | Chin et al. |
| 5,445,615 A | 8/1995 | Yoon |
| 5,468,248 A | 11/1995 | Chin et al. |
| 5,514,091 A | 5/1996 | Yoon |
| 5,514,153 A | 5/1996 | Bonutti |
| 5,540,658 A | 7/1996 | Evans et al. |
| 5,540,711 A | 7/1996 | Kieturakis et al. |
| 5,607,441 A | 3/1997 | Sierocuk et al. |
| 5,607,443 A | 3/1997 | Kieturakis et al. |
| 5,632,761 A | 5/1997 | Smith et al. |
| 5,656,013 A | 8/1997 | Yoon |
| 5,667,479 A | 9/1997 | Kieturakis |
| 5,667,520 A | 9/1997 | Bonutti |
| 5,704,372 A | 1/1998 | Moll et al. |
| 5,707,382 A | 1/1998 | Sierocuk et al. |
| 5,713,869 A | 2/1998 | Morejon |
| 5,722,986 A | 3/1998 | Smith et al. |
| 5,728,119 A | 3/1998 | Smith et al. |
| 5,730,748 A | 3/1998 | Fogarty et al. |
| 5,730,756 A | 3/1998 | Kieturakis et al. |
| 5,738,628 A | 4/1998 | Sierocuk et al. |
| 5,755,693 A | 5/1998 | Walker et al. |
| 5,762,604 A | 6/1998 | Kieturakis |
| 5,772,680 A | 6/1998 | Kieturakis et al. |
| 5,779,728 A | 7/1998 | Lunsford et al. |
| 5,797,947 A | 8/1998 | Mollenauer |
| 5,803,901 A | 9/1998 | Chin et al. |
| 5,810,867 A | 9/1998 | Zarbatany et al. |
| 5,814,060 A | 9/1998 | Fogarty et al. |
| 5,836,913 A | 11/1998 | Orth et al. |
| 5,836,961 A | 11/1998 | Kieturakis et al. |
| 5,865,802 A | 2/1999 | Yoon et al. |
| 5,893,866 A | 4/1999 | Hermann et al. |
| 5,925,058 A | 7/1999 | Smith et al. |
| 6,361,543 B1 | 3/2002 | Chin et al. |
| 6,368,337 B1 | 4/2002 | Kieturakis et al. |
| 6,375,665 B1 | 4/2002 | Nash et al. |
| 6,379,372 B1 | 4/2002 | Dehdashtian et al. |
| 6,432,121 B1 | 8/2002 | Jervis |
| 6,447,529 B2 | 9/2002 | Fogarty et al. |
| 6,468,205 B1 | 10/2002 | Mollenauer et al. |
| 6,506,200 B1 | 1/2003 | Chin |
| 6,514,272 B1 | 2/2003 | Kieturakis et al. |
| 6,517,514 B1 | 2/2003 | Campbell |
| 6,527,787 B1 | 3/2003 | Fogarty et al. |
| 6,540,764 B1 | 4/2003 | Kieturakis et al. |
| 6,796,960 B2 | 9/2004 | Cioanta et al. |
| 8,454,645 B2 | 6/2013 | Criscuolo et al. |
| 2004/0116894 A1 | 6/2004 | DeLegge |
| 2004/0230218 A1* | 11/2004 | Criscuolo ......... A61B 17/3421 |
| | | 606/190 |
| 2010/0081990 A1* | 4/2010 | Swisher ............ A61B 17/3421 |
| | | 604/101.05 |
| 2018/0271557 A1* | 9/2018 | Buyda ............... A61B 17/3423 |

(56) References Cited

U.S. PATENT DOCUMENTS

2019/0059937 A1\* 2/2019 Buyda ................ A61B 17/3423
2020/0107859 A1 4/2020 Zhu

FOREIGN PATENT DOCUMENTS

| | | |
|---|---|---|
| EP | 0880939 A1 | 12/1998 |
| WO | 9206638 A1 | 4/1992 |
| WO | 9218056 A1 | 10/1992 |
| WO | 9221293 A1 | 12/1992 |
| WO | 9221295 A1 | 12/1992 |
| WO | 9309722 A1 | 5/1993 |
| WO | 9721461 A1 | 6/1997 |
| WO | 9912602 A1 | 3/1999 |
| WO | 0126724 A2 | 4/2001 |
| WO | 02096307 A2 | 12/2002 |
| WO | 2004032756 A2 | 4/2004 |

\* cited by examiner

SURGICAL ACCESS ASSEMBLY HAVING PRE-FILLED AIR CHAMBER

FIELD

The present technology is generally related to surgical access devices and more particularly to a surgical access assembly having a pre-filled fluid chamber that is adjustable by a set of collars for use in a minimally invasive surgical procedure.

BACKGROUND

Minimally invasive surgical procedures including both endoscopic and laparoscopic procedures permit surgery to be performed on organs, tissues, and vessels far removed from an opening within the tissue. In laparoscopic procedures, the abdominal cavity is insufflated with an insufflation fluid, e.g., $CO_2$, to create a pneumoperitoneum thereby providing access to the underlying organs. A laparoscopic instrument is introduced through a cannula accessing the abdominal cavity to perform one or more surgical tasks. An interior of the cannula usually includes a seal to establish a substantially fluid-tight seal about the instrument to preserve the integrity of the pneumoperitoneum.

While minimally invasive surgical procedures have proven to be quite effective in surgery, several limitations remain. For example, the cannula, which is subjected to the pressurized environment, i.e., the pneumoperitoneum, may exhibit a tendency to back out of the incision in the abdominal wall particularly during manipulation of the instrument within the cannula. Conventional cannulas may incorporate an inflatable balloon at the end of the cannula in an effort to resist withdrawal of the cannula from the tissue site. Typically, pumps or syringes containing air are coupled to the cannula and actuated to either inflate or deflate the balloon.

SUMMARY

The present disclosure relates to a surgical access assembly including a balloon cannula for providing access to a surgical cavity within a patient (e.g., an abdominal cavity) having a collar coupled to the balloon cannula for inflating a balloon of the balloon cannula via a pre-filled air chamber.

In one aspect, the present disclosure provides a surgical access assembly including an elongated cannula member having a proximal end portion and a distal end portion, a balloon anchor coupled to the distal end portion of the elongated cannula member, a sleeve of the balloon anchor extending proximally along an outer surface of the elongated cannula member, a chamber defined between the sleeve of the balloon anchor and the outer surface of the elongated cannula member, and a first collar coupled to the elongated cannula member. The first collar is slidable along the elongated cannula member and engageable with the sleeve of the balloon anchor.

In aspects, a second collar is disposed proximal to the first collar and coupled to the elongated cannula member, the second collar is slidable along the elongated cannula member and engageable with the sleeve of the balloon anchor.

In aspects, the chamber may be a pre-filled with fluid.

In aspects, the first collar may be translated distally along the elongated cannula member from a first position at the proximal end portion to a second position at the distal end portion.

In aspects, translating the first collar towards the second position may cause the fluid to be transferred from the chamber to the balloon anchor thereby expanding the balloon anchor.

In aspects, the second collar may be translated distally along the elongated cannula member towards the second position of the first collar until the second collar abuts the first collar.

In aspects, the second collar may be configured to prevent proximal movement of the first collar.

In aspects, translating the second collar towards the first position may deflate the balloon anchor.

In aspects, the first collar may be translated proximally along the elongated cannula member towards the first position causing the fluid to be transferred from the balloon anchor to the chamber.

In aspects, the surgical access assembly may further include a cannula housing coupled to the proximal end portion of the elongated cannula member.

In another aspect, the disclosure provides a method of actuating a balloon anchor of a surgical access assembly including sliding a first collar distally along an elongated cannula member of the surgical access assembly and engaging the first collar with the sleeve such that a fluid in a chamber is transferred to the balloon anchor thereby expanding the balloon anchor. The surgical access assembly includes a balloon anchor disposed in a distal region thereof, the balloon anchor having a sleeve extending proximally along an outer surface of the elongated cannula member defining a chamber therebetween.

In aspects, the method may further include sliding a second collar distally along the elongated cannula member of the surgical access assembly such that the second collar abuts the first collar thereby inhibiting proximal movement of the first collar.

In aspects, the method may further include sliding the second collar proximally along the elongated cannula member to retreat from the first collar thereby allowing proximal movement of the first collar and sliding the first collar proximally along the elongated cannula member towards the second collar thereby deflating the balloon anchor.

In aspects, engagement of the first collar with the sleeve may collapse the sleeve.

DETAILED DESCRIPTION

Figure 1A:
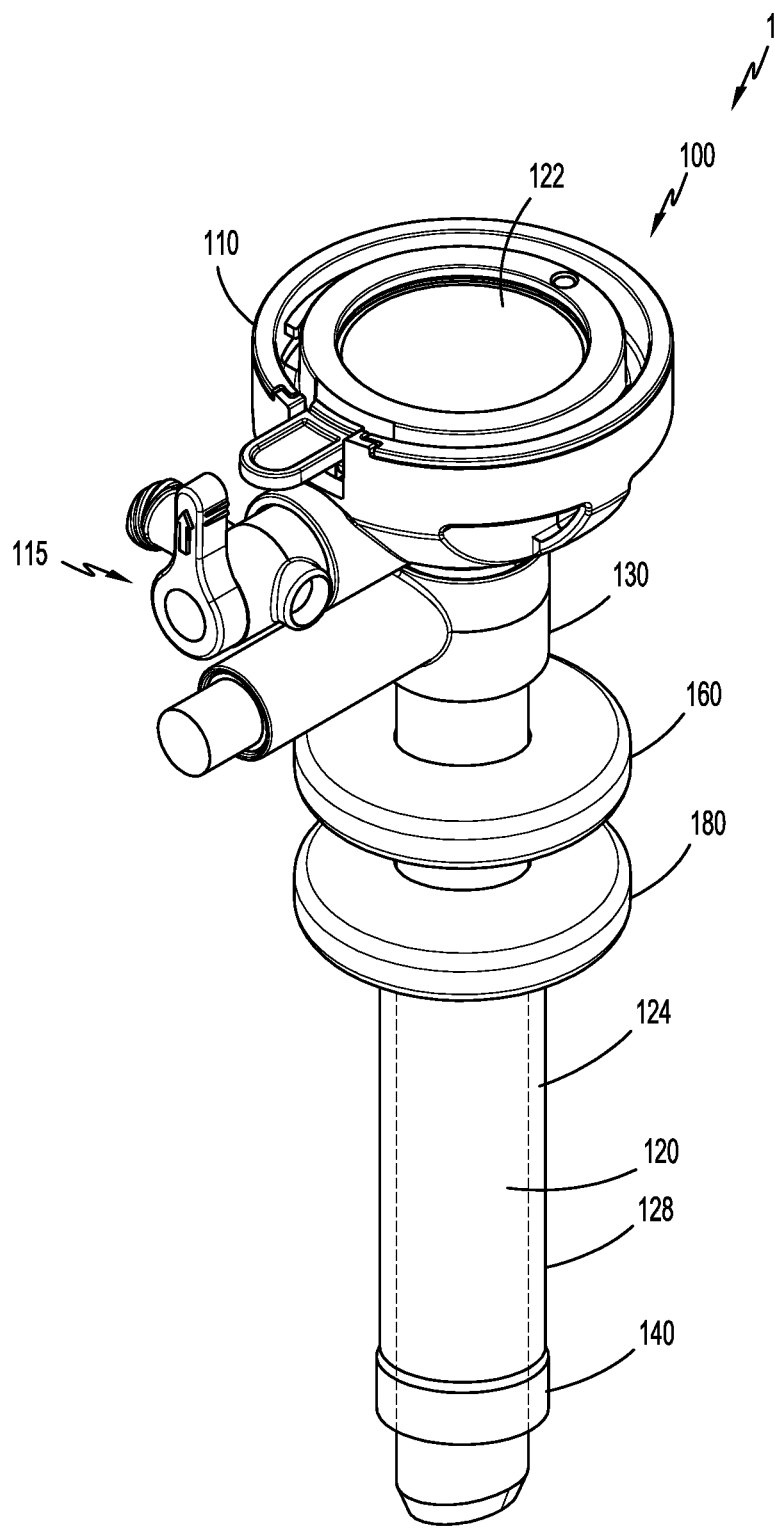
FIG. 1A is a perspective view of a surgical access assembly according to an aspect of the disclosure including a cannula, a valve, top and bottom movable collars, and a balloon anchor.

Embodiments of the presently disclosed surgical access assembly are described in detail with reference to the drawings, in which like reference numerals designate identical or corresponding elements in each of the several views. As used herein, the term "distal" refers to that portion of the surgical access assembly or component thereof, farther from the user, while the term "proximal" refers to that portion of the surgical access assembly, or component thereof, closer to the user.

As used herein, the term "clinician" refers to a doctor, nurse, surgeon, or other care provider and may include support personnel. In the following description, well-known functions, or construction are not described in detail to avoid obscuring the disclosure in unnecessary detail.

In general, the present disclosure provides a surgical access assembly having top and bottom movable collars, a collapsible outer sleeve, and an elongated cannula member, the collapsible outer sleeve and the elongated cannula member define a chamber therebetween that is pre-filled with a fluid for use with a balloon anchor. Upon distal translation of the bottom movable collar, the pre-filled fluid is forced distally towards the balloon anchor. Upon distal translation of the top movable collar, the fluid in the balloon of the balloon anchor is maintained. Upon proximal translation of the top and bottom movable collars, the fluid may be released from the balloon of the balloon anchor. In this way, a clinician may no longer need to attach an extra component, such as, for example a syringe or pump, to the balloon anchor to inflate or deflate the balloon of the balloon anchor.

Referring initially to FIG. 1A, which illustrates a surgical access assembly 1 that generally includes a surgical access assembly or cannula assembly 100, having a top movable collar or top collar 160 and a bottom movable collar or bottom collar 180 for use with the cannula assembly 100. The cannula assembly 100 is intended to permit access to an insufflated abdominal cavity during a laparoscopic procedure to permit the introduction of a surgical instrument for performing various surgical tasks on internal organs within the cavity. The surgical instrument may be a surgical instrument such as laparoscopic or endoscopic clip appliers, graspers, dissectors, retractors, staplers, laser probes, photographic devices, tubes, endoscopes and laparoscopes, electro-surgical devices and the like. An obturator (not explicitly shown) may be positioned in the cannula assembly 100 to facilitate access to the abdominal cavity. The obturator may be any conventional obturator having a penetrating tip configured to penetrate tissue.

The cannula assembly 100 includes a cannula housing 110, an elongated cannula member 120 extending distally from the cannula housing 110, a valve 130, and an expandable member or balloon anchor 140 formed with a collapsible outer sleeve or sleeve 128. The cannula housing 110 is dimensioned for engagement by the clinician and may include or more internal seals (not shown) adapted to establish a seal about a surgical instrument introduced therethrough. The cannula housing 110 also may include an insufflation connector 115 (e.g., a luer connector) for connecting to a source of insufflation fluid (not shown) for delivery within, e.g., the abdominal cavity. The elongated cannula member 120 defines a longitudinal passageway 122 to permit passage of the surgical instrument. The longitudinal passageway 122 is also in fluid communication with the insufflation connector 115 to convey insufflation fluids into the abdominal cavity to establish and/or maintain the pneumoperitoneum.

Figure 2:
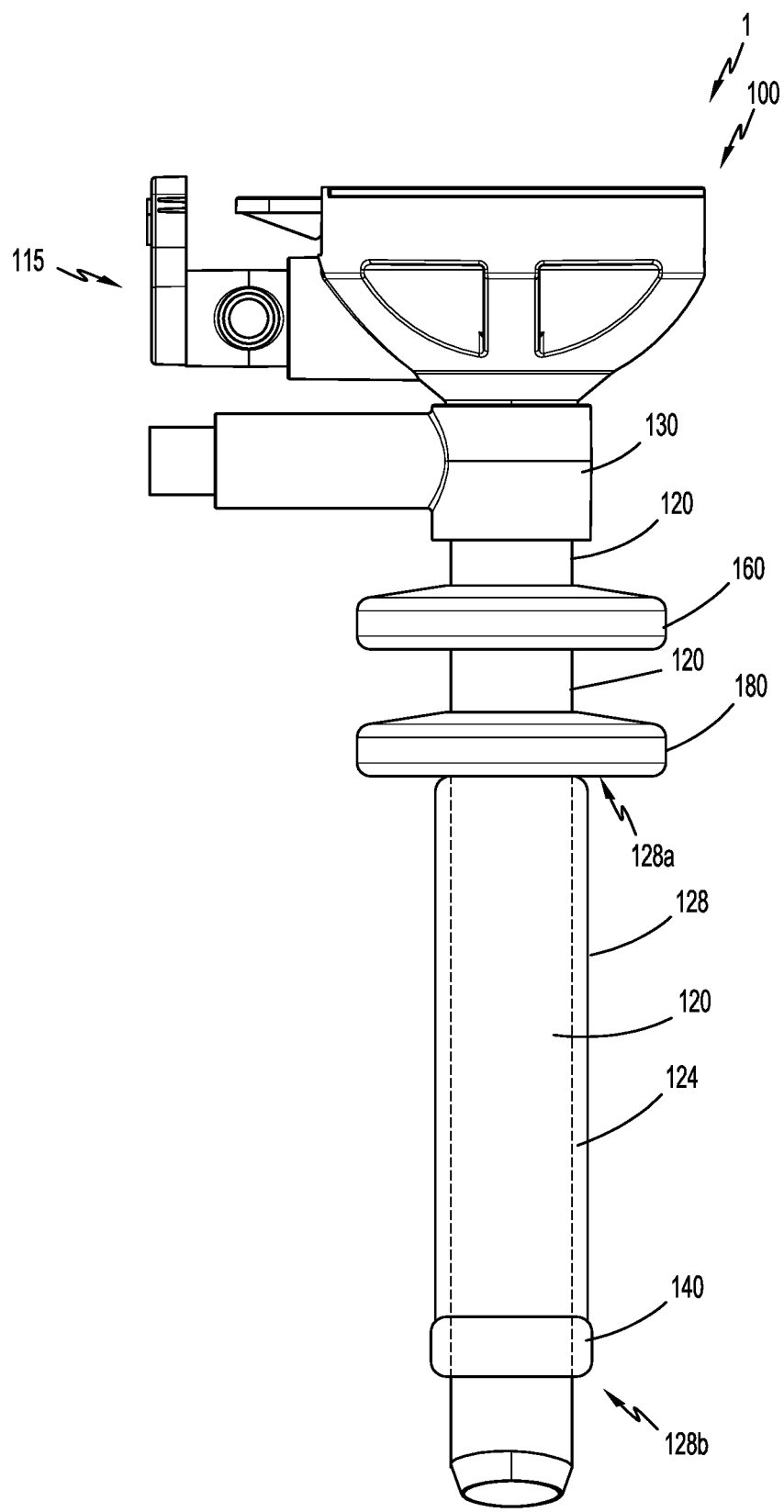
FIG. 2 is a side view of the surgical access assembly of FIG. 1A.

With reference to FIG. 2, the bottom collar 180 of the cannula assembly 100 includes an inner portion dimensioned to slidably receive both the elongated cannula member 120 and a first end portion 128a of the sleeve 128. The bottom collar 180 is slidable along the elongated cannula member 120 to adjust the height of the bottom collar 180 and engage the sleeve 128 of the balloon anchor 140 along the elongated cannula member 120.

The top collar 160 of the cannula assembly 100 includes an inner portion dimensioned to slidably receive the elongated cannula member 120 and a portion of the sleeve 128. The top collar 160 is slidable along the elongated cannula member 120 to inhibit proximal movement of the bottom collar 180. In aspects, the top collar 160 may be releasably engageable, i.e., lockable, along the elongated cannula member 120 to retain position of the top collar 160 and thereby act as a limit stop for proximal movement of the bottom collar 180.

The sleeve 128 includes the first end portion 128a and a second end portion 128b with the second end portion 128b of the sleeve 128 extending from the balloon anchor 140 proximally along an outer surface of the elongated cannula member 120 to the first end portion 128a along the proximal end portion of the elongated cannula member 120 defining a fluid-tight seal or a chamber 124. The chamber 124 is configured to store a fluid (e.g., air) and may be pre-filled with a set amount of the fluid.

Figure 1B:
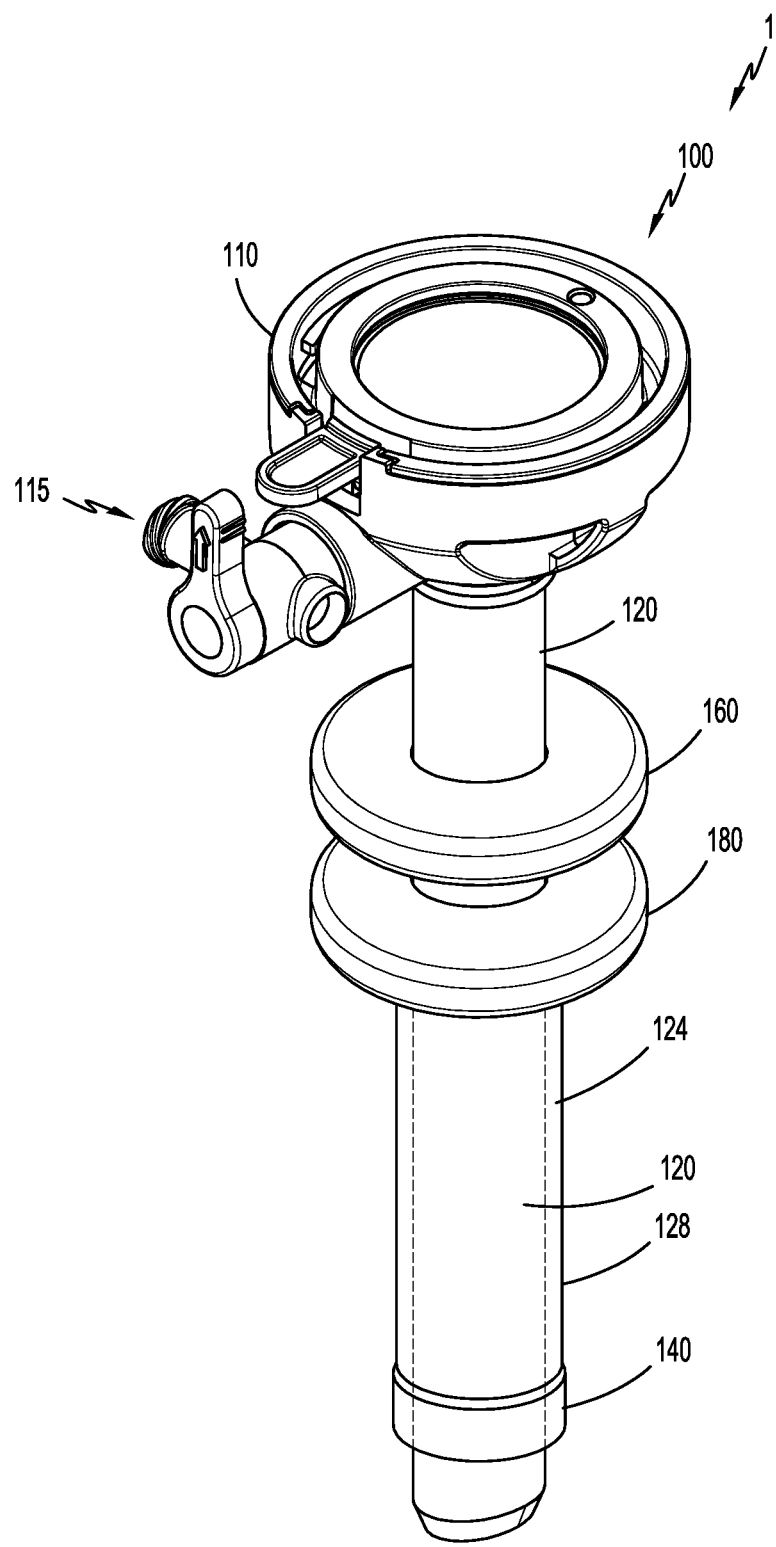
FIG. 1B is a perspective view of the surgical access assembly, with the valve removed according to another aspect of the disclosure.

With quick reference to FIG. 1B, the cannula assembly 100 may not include the valve 130. The top and bottom collar 160, 180 may be positioned closer to the cannula housing 110 and the first end portion 128a of the sleeve 128 may form a fluid-tight seal closer to the cannula housing 110 on the elongated shaft, thus providing for additional amount of the fluid within the chamber 124 and more control of height adjustment and the fluid pressure within the balloon anchor 140.

In operation, the surgical access assembly 1 may be used in a minimally invasive surgery to provide access to an underlying cavity, e.g., an abdominal cavity. In one methodology, the abdominal cavity 30 is insufflated to establish a pneumoperitoneum. The obturator is positioned within the cannula assembly 100 and the assembled unit is advanced, while the balloon anchor 140 is in a deflated state, through a layer of tissue 10, until the top collar 180 engages the first layer of tissue 10 (FIG. 3).

Figure 3:
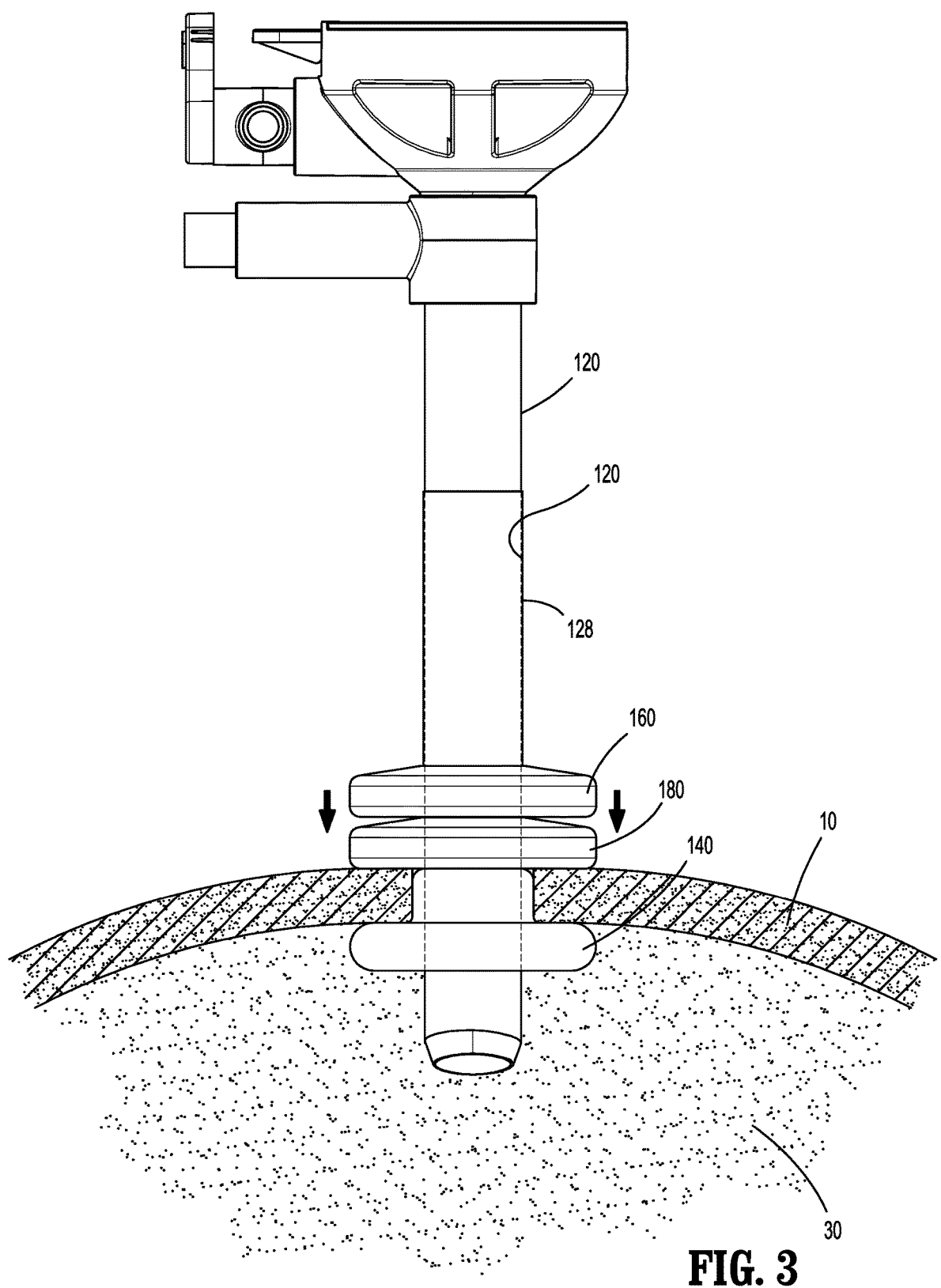
FIG. 3 is a side view of the surgical access assembly of FIG. 1A, wherein the surgical access assembly is inserted into a patient and the balloon anchor is inflated.

Referring to FIGS. 2 and 3, upon positioning the balloon anchor 140 adjacent the abdominal wall, the bottom collar 180 is slid distally along the elongated cannula member 120 until to the bottom collar 180 is set at a desired height. Upon sliding of the bottom collar 180, the bottom collar 180 engages the sleeve 128 thereby collapsing the sleeve 128 and transferring fluid in the chamber 124 to the balloon anchor 140. The fluid supplied to the balloon anchor 140 causes the balloon anchor 140 to expand and inflate (FIG. 3). Once fluid is supplied to the balloon anchor 140, the top collar 160 is slid distally until the top collar 160 abuts the bottom collar 180, thereby inhibiting proximal movement of the bottom collar 180. Thus, fluid pressure is maintained in the balloon anchor 140 via the top and bottom collars 160, 180, which prevents the fluid pressure from escaping the balloon anchor 140 back into the chamber 124.

To deflate and withdraw the cannula assembly 100 from the abdominal cavity 30, while minimizing damage to the tissue layer 10, the top collar 160 is slid proximally towards the cannula housing 110 to retreat from the bottom collar 180, thereby allowing proximal movement of the bottom collar 180. The bottom collar 180 is slid proximally towards the top collar 160, and the cannula assembly 110 is slowly withdrawn from the abdominal cavity through the tissue layer thereby transferring fluid from the balloon anchor 140 into the chamber 124 causing the sleeve 128 to expand and the balloon anchor 140 to fully deflate or at least partially deflate. Once deflated, the cannula assembly 100 may be fully withdrawn from the abdominal cavity 30 through the tissue layer 10.

It should be understood that various aspects disclosed herein may be combined in different combinations than the combinations specifically presented in the description and accompanying drawings. It should also be understood that, depending on the example, certain acts or events of any of the processes or methods described herein may be performed in a different sequence, may be added, merged, or left out altogether (e.g., all described acts or events may not be necessary to carry out the techniques). In addition, while certain aspects of this disclosure are described as being performed by a single module or unit for purposes of clarity, it should be understood that the techniques of this disclosure may be performed by a combination of units or modules associated with, for example, a medical device.

What is claimed is:

1. A surgical access assembly comprising:
    an elongated cannula member having a proximal end portion and a distal end portion;
    a balloon anchor coupled to the distal end portion of the elongated cannula member, a sleeve of the balloon anchor extending proximally along an outer surface of the elongated cannula member;
    a chamber defined between the sleeve of the balloon anchor and the outer surface of the elongated cannula member, the chamber being pre-filled with a fluid;
    a first collar coupled to the elongated cannula member, the first collar slidable along the elongated cannula member and engageable with the sleeve of the balloon anchor, the first collar translatable from a first position at the proximal end portion towards a second position at the distal end portion, wherein translation of the first collar towards the distal end portion causes the fluid to be transferred from the chamber to the balloon anchor thereby expanding the balloon anchor; and
    a second collar disposed proximal to the first collar and coupled to the elongated cannula member, the second collar slidable along the elongated cannula member and engageable with the sleeve of the balloon anchor.

2. The surgical access assembly of claim 1, wherein the second collar is translated distally along the elongated cannula member towards the second position of the first collar until the second collar abuts the first collar.

3. The surgical access assembly of claim 2, wherein translating the second collar towards the first position of the first collar deflates the balloon anchor.

4. The surgical access assembly of claim 3, wherein the first collar is translated proximally along the elongated cannula member towards the first position causing the fluid to be transferred from the balloon anchor to the chamber.

5. The surgical access assembly of claim 1, wherein the second collar is configured to prevent proximal movement of the first collar.

6. The surgical access assembly of claim 1, further including a cannula housing coupled to the proximal end portion of the elongated cannula member.

7. A method of actuating a balloon anchor of a surgical access assembly comprising:
    sliding a first collar distally along an elongated cannula member of the surgical access assembly from a proximal region of the elongated cannula member towards a distal region of the elongated cannula member, the surgical access assembly including a balloon anchor disposed in the distal region of the elongated cannula member, the balloon anchor having a sleeve extending proximally along an outer surface of the elongated cannula member defining a chamber between the sleeve and the outer surface;
    engaging the first collar with the sleeve such that a fluid in the chamber is transferred to the balloon anchor as the first collar slides towards the distal region thereby expanding the balloon anchor; and
    sliding a second collar distally along the elongated cannula member of the surgical access assembly, the second collar located proximally of the first collar.

8. The method of claim 7, further including:
    sliding the second collar distally along the elongated cannula member of the surgical access assembly such that the second collar abuts the first collar thereby inhibiting proximal movement of the first collar.

9. The method of claim 8, further including:
    sliding the second collar proximally along the elongated cannula member to retreat from the first collar thereby allowing proximal movement of the first collar; and
    sliding the first collar proximally along the elongated cannula member towards the second collar thereby deflating the balloon anchor.

10. The method of claim 8, wherein engagement of the first collar with the sleeve collapses the sleeve.

11. A surgical access assembly comprising:
    an elongated cannula member having a proximal end portion and a distal end portion;
    a balloon anchor coupled to the distal end portion and having a sleeve extending proximally along an outer surface of the elongated cannula member;
    a chamber defined between the sleeve and the outer surface;
    a first collar coupled to the elongated cannula member and engageable with the sleeve, the first collar slidable along the elongated cannula member between the proximal end portion and the distal end portion such that translation of the first collar towards the distal end portion causes a fluid to be transferred from the chamber to the balloon anchor thereby expanding the balloon anchor; and
    a second collar coupled to the elongated cannula member and disposed proximally of the first collar, the second collar being slidable along the elongated cannula member and engageable with the sleeve of the balloon anchor.

12. The surgical access assembly of claim 11, wherein the second collar is translatable distally along the elongated cannula member towards the distal end portion until the second collar abuts the first collar.

13. The surgical access assembly of claim 12, wherein the second collar is translatable towards the proximal end portion and is configured to deflate the balloon anchor.

14. The surgical access assembly of claim 11, wherein the second collar is configured to inhibit proximal movement of the first collar.

15. The surgical access assembly of claim 11, further including a cannula housing coupled to the proximal end portion.

* * * * *